(12) United States Patent
Watanabe et al.

(10) Patent No.: US 10,527,578 B2
(45) Date of Patent: Jan. 7, 2020

(54) CERAMIC HEATER, SENSOR ELEMENT, AND GAS SENSOR

(71) Applicant: NGK INSULATORS, LTD., Nagoya-shi, Aichi (JP)

(72) Inventors: Yusuke Watanabe, Nagoya (JP); Takao Murase, Konan (JP); Masashi Yasui, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 0 days.

(21) Appl. No.: 15/238,855

(22) Filed: Aug. 17, 2016

(65) Prior Publication Data
US 2017/0052144 A1 Feb. 23, 2017

(30) Foreign Application Priority Data

Aug. 21, 2015 (JP) .................................. 2015-164211

(51) Int. Cl.
*H05B 3/00* (2006.01)
*G01N 27/406* (2006.01)
(Continued)

(52) U.S. Cl.
CPC ....... *G01N 27/4067* (2013.01); *H05B 1/0247* (2013.01); *H05B 3/0014* (2013.01); *H05B 3/265* (2013.01)

(58) Field of Classification Search
CPC .............. B23K 9/0286; G01N 27/407; G01N 27/4067; H05B 1/0247; H05B 3/0014; H05B 3/265
(Continued)

(56) References Cited

U.S. PATENT DOCUMENTS 3,778,744 A * 12/1973 Brandi ..................... H01C 1/14
338/260
4,384,192 A * 5/1983 Lowell ..................... H05B 3/10
219/465.1
(Continued)

FOREIGN PATENT DOCUMENTS

EP  2 107 364 A1  10/2009
JP  4-329289 A  11/1992
(Continued)

OTHER PUBLICATIONS

The Official Communication of the Third Party Observations for the corresponding German patent application No. 10 2016 215 507.5, dated Dec. 14, 2017.
(Continued)

*Primary Examiner* — Tu B Hoang
*Assistant Examiner* — Masahiko Muranami
(74) *Attorney, Agent, or Firm* — Global IP Counselors, LLP (57) ABSTRACT

A heater section includes a plate-like ceramic body (a first substrate layer 1, a second substrate layer 2, and a third substrate layer 3) having a longitudinal direction (front-rear direction) and a short-length direction (left-right direction), and a heater 72 disposed within the plate-like ceramic body and including a lead section 79 and a heating section 76 connected to the lead section 79. The heating section 76 includes a straight portion 78 extending along the longitudinal direction, and a lead side curved portion 77b connected to one of the ends of the straight portion 78 closer to the lead section 79. The lead side curved portion 77b has a lower resistance per unit length than the straight portion 78 at one or more temperatures in the range of 700° C. to 900° C.

11 Claims, 4 Drawing Sheets

(51) Int. Cl.
*H05B 1/02* (2006.01)
*H05B 3/26* (2006.01)

(58) Field of Classification Search
USPC ....... 219/544, 541, 209, 552, 553, 543, 781,
219/270, 267, 505, 548, 228, 229, 443.1,
219/474, 475, 478, 481, 542, 536, 538,
219/203; 338/306, 307, 308, 314, 249,
338/254, 280, 281, 283, 291, 293, 7, 211;
392/465, 485, 490, 500; 204/408, 425,
204/426, 781
See application file for complete search history.

(56) References Cited

U.S. PATENT DOCUMENTS

| | | | | |
|---|---|---|---|---|
| 4,733,056 | A | * | 3/1988 | Kojima .................. H05B 3/283 219/270 |
| 5,444,228 | A | * | 8/1995 | Gelus ...................... D06F 75/24 219/528 |
| 5,895,591 | A | * | 4/1999 | Kojima ............. G01N 27/4067 204/426 |
| 6,169,275 | B1 | * | 1/2001 | Noda ..................... H05B 3/141 219/542 |
| 2005/0199610 | A1 | * | 9/2005 | Ptasienski ................ H05B 3/26 219/543 |
| 2008/0223849 | A1 | | 9/2008 | Naito et al. |
| 2009/0250344 | A1 | * | 10/2009 | Ohya ................. G01N 27/4067 204/425 |
| 2014/0102170 | A1 | | 4/2014 | Kato |

FOREIGN PATENT DOCUMENTS

| | | |
|---|---|---|
| JP | H11-304744 A | 11/1999 |
| JP | 2009-265085 A | 11/2009 |
| JP | 4826461 B2 | 9/2011 |
| WO | 2013/005491 A1 | 1/2013 |

OTHER PUBLICATIONS

Third Party Submission dated Jun. 20, 2019 in correspond Japanese Patent Application No. 2015-164211 (with English Translation).

* cited by examiner

CERAMIC HEATER, SENSOR ELEMENT, AND GAS SENSOR

BACKGROUND OF THE INVENTION

1. Field of the Invention

The present invention relates to a ceramic heater, a sensor element, and a gas sensor.

2. Description of the Related Art

There has been known ceramic heaters including a ceramic sheet and a heater pattern that is folded a plurality of times in the longitudinal direction of the ceramic sheet (for example, PTL 1). The heater pattern disclosed in PTL 1 includes straight conducting segments extending along the longitudinal direction, a curved conducting segment connecting the straight conducting segments, and a pair of electricity conducting patterns.

CITATION LIST

Patent Literature

PTL 1: Japanese Patent No. 4826461

SUMMARY OF THE INVENTION

Some of the ceramic heaters contain an alkali metal or an alkaline-earth metal. When the heating element heats, such a metal is likely to be cationized and thus to be attracted to the low-potential side. Also, oxygen or any other element bound to the alkali metal or alkaline-earth metal may be ionized into anion and thus to be attracted to the high-potential side. These phenomena are called migration. In a case, ions moved by migration react with the heating element, thereby degrading the heating element in such a manner that a line of the pattern is thinned or broken.

The present invention is intended to solve this problem, and a major object of the invention is to prevent degradation of the heating element resulting from migration.

In order to achieve the major object, the following is provided.

A ceramic heater of the present invention includes:

a plate-like ceramic body having a longitudinal direction and a short-length direction; and a heating element disposed within the plate-like ceramic body, the heating element including a lead section and a heating section connected to the lead section, wherein the heating section includes a straight portion whose length direction is along the longitudinal direction and at least one lead side curved portion connected to one of the ends of the straight portion closer to the lead section, and wherein the closest to the lead section of the at least one lead side curved portion has a lower resistance per unit length than the straight portion at one or more temperatures in the range of 700° C. to 900° C.

In the first ceramic heater, the heating section includes the straight portion and the lead side curved portion. The closest to the lead section of the at least one lead side curved portion has a lower resistance per unit length than the straight portion at one or more temperatures in the range of 700° C. to 900° C. Thus, the closest lead side curved portion to the lead section has a lower heating density (quantity of heat generation per unit length) than the straight portion at one or more temperatures in the range of 700° C. to 900° C., and accordingly, the temperature increase of this curved portion is suppressed. In general, since the closest lead side curved portion is close to the lead section, the region between the closest lead side curved portion and the lead section tends to have a large potential gradient, and thus migration is likely to occur. In addition, alkali metals, alkaline-earth metals, and the like are more likely to ionize as temperature increases. In the first ceramic heater of the present invention, ionization is prevented by suppressing the temperature increase of the closest lead side curved portion to the lead section, in which migration is liable to occur. Thus, at least one of the closest lead side curved portion and the lead section can be prevented from being degraded by migration. Consequently, the degradation of the heating element is reduced.

A second ceramic heater of the present invention includes:

a plate-like ceramic body having a longitudinal direction and a short-length direction; and a heating element disposed within the plate-like ceramic body, the heating element including a lead section having a positive lead and a heating section connected to the lead section.

The heating section includes a straight portion that are arranged along the longitudinal direction and whose length direction is along the longitudinal direction of the plate-like ceramic body, and at least one lead side curved portion connected to one of the ends of the straight portion closer to the lead section. The closest to the positive lead of the at least one lead side curved portion has a lower resistance per unit length than the straight portion at one or more temperatures in the range of 700° C. to 900° C.

In the second ceramic heater, the heating section includes a straight portion and at least one lead side curved portion. The closest to the positive lead of the at least one lead side curved portion has a lower resistance per unit length than the straight portion at one or more temperatures in the range of 700° C. to 900° C. Thus, the closest lead side curved portion to the positive lead has a lower heating density than the straight portion at one or more temperatures in the range of 700° C. to 900° C., and accordingly, the temperature increase of this curved portion is suppressed. In general, since the closest lead side curved portion is close to the positive lead, the region between the closest lead side curved portion and the positive lead tends to have a large potential gradient, and thus migration is likely to occur. In addition, alkali metals, alkaline-earth metals, and the like are more likely to ionize as temperature increases. In the second ceramic heater of the present invention, ionization is prevented by suppressing the temperature increase of the closest lead side curved portion to the positive lead, in which migration is liable to occur. Thus, at least one of the closest lead side curved portion and the lead section can be prevented from being degraded by migration. Consequently, the degradation of the heating element is reduced.

In the first and the second ceramic heater, the ratio R1/R2 of unit resistance R1 [μΩ/mm] being the resistance per unit length of the closest lead side curved portion to unit resistance R2 [μΩ/mm] being the resistance per unit length of the straight portion may be 0.87 or less at one or more temperatures in the above temperature range. Thus, the degradation of the heating element resulting from migration can be further reduced. Preferably, the unit resistance ratio R1/R2 is 0.80 or less at one or more temperatures in the above temperature range.

In the first and the second ceramic heater, the cross section of the closest lead side curved portion, taken in the direction perpendicular to the length direction thereof may have a larger area than that of the straight portion. Thus, the resistance per unit length of the closest lead side curved portion tends to be lower than that of the straight portion. In this instance, preferably, the ratio S2/S1 of the area S2 [mm$^2$] of the cross section of the straight portion taken in the direction perpendicular to the length direction thereof to the area S1 [mm$^2$] of the cross section of the closest lead side curved portion taken in the direction perpendicular to the length direction thereof is 0.87 or less. Thus, the unit resistance ratio R1/R2 tends to be 0.87 or less at one or more temperatures in the above temperature range. More preferably, the cross-sectional area ratio S2/S1 is 0.80 or less.

In the first and the second ceramic heater, the closest lead side curved portion may have a lower volume resistivity than the straight portions at one or more temperatures in the above temperature range. Thus, the resistance per unit length of the closest lead side curved portion tends to be lower than that of the straight portion. In this instance, preferably, the ratio ρ1/ρ2 of the volume resistivity ρ1 [μΩ·cm] of the closest lead side curved portion to the volume resistivity ρ2 [μΩ·cm] of the straight portion is 0.87 or less at one or more temperatures in the above temperature range. Thus, the unit resistance ratio R1/R2 tends to be 0.87 or less at one or more temperatures in the above temperature range. More preferably, the volume resistivity ratio ρ1/ρ2 is 0.80 or less at one or more temperatures in the above temperature range.

In the first and the second ceramic heater, the heating section may have four or more straight portions arranged along the short-length direction of the plate-like ceramic body. In this structure, the at least one lead side curved portion connects a pair of the straight portions adjacent to each other in the short-length direction at one of the ends of each adjacent straight portion closer to the lead section, and the heating section includes a plurality of non-lead side curved portions, each connecting a pair of the straight portions adjacent to each other in the short-length direction at one of the ends of each adjacent straight portion far from the lead section.

A sensor element according to the present invention includes the first or the second ceramic heater according to any of the above-described embodiments.

The sensor element is used to detect the concentration of a specific gas in a measurement-object gas.

Since the sensor element includes the ceramic heater of any of the above-described embodiments, the sensor element can produce the same effect as the first and the second ceramic heater, for example, the effect of reducing the degradation of the heating element caused by migration.

A gas sensor of the present invention includes the above-described sensor element.

Since the sensor includes the sensor element including the ceramic heater of any of the above-described embodiments, the sensor can produce the same effect as the ceramic heater and the sensor element of the present invention, for example, the effect of reducing the degradation of the heating element caused by migration.

DETAILED DESCRIPTION OF THE INVENTION

Figure 1:
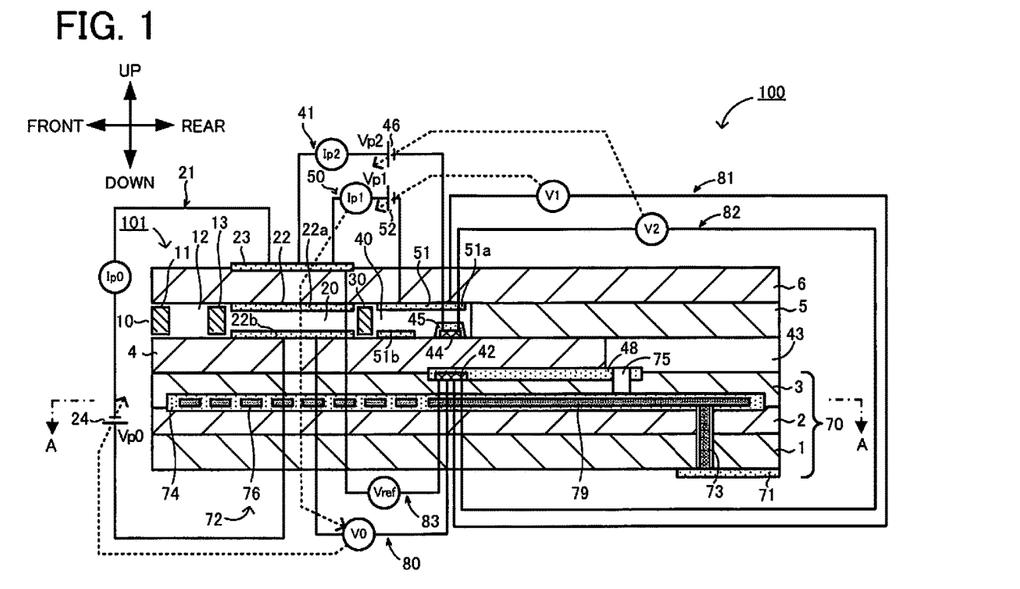
FIG. 1 is a schematic sectional view of an example of the structure of a gas sensor 100.
Figure 2:
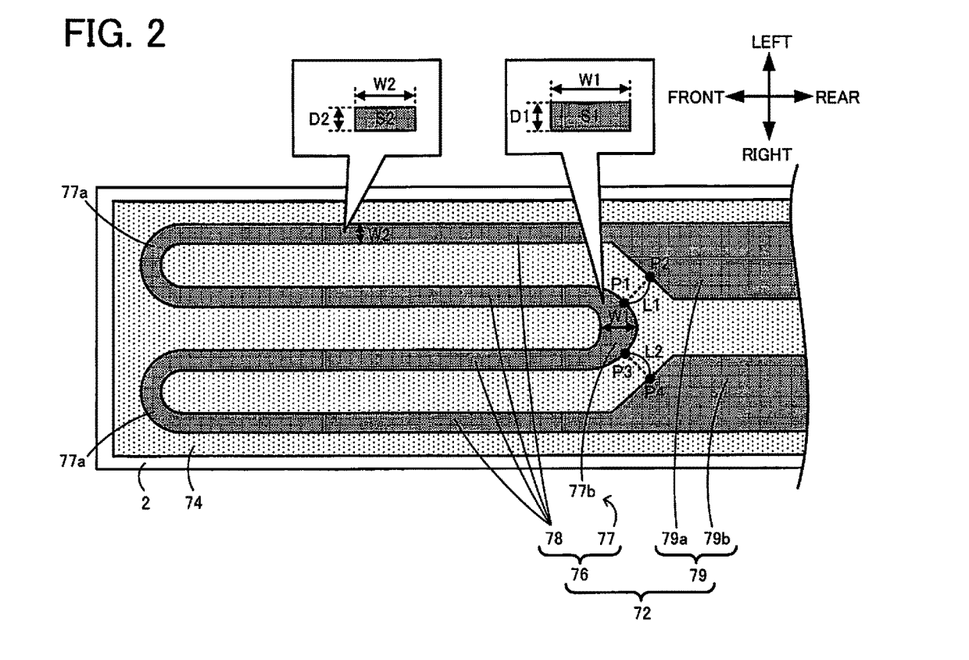
FIG. 2 is a sectional view taken along line A-A in FIG. 1.

Embodiments of the present invention will now be described with reference to the drawings. FIG. 1 is a schematic sectional view of an example of the structure of a gas sensor 100 of an embodiment of the present invention. FIG. 2 is a sectional view taken along line A-A in FIG. 1. The gas sensor 100 is such that a sensor element 101 therein detects the concentration of a specific gas, such as NOx gas, in a measurement-object gas, such as exhaust gas from automobiles. The sensor element 101 is in the shape of a long rectangular parallelepiped. The longitudinal direction (lateral direction in FIG. 1) of this sensor element 101 is defined as the front-rear direction, and the thickness direction (vertical direction in FIG. 1) of the sensor element 101 is defined as the vertical direction. The width direction (perpendicular to the front-rear direction and the vertical direction) of the sensor element 101 is defined as the left-right direction.

The sensor element 101 has a multilayer structure defined by a stack of six oxygen ion conductive solid electrolyte layers made of, for example, zirconia (ZrO$_2$) that are a first substrate layer 1, a second substrate 2, a third substrate layer 3, a first solid electrolyte layer 4, a spacer layer 5, and a second solid electrolyte layer 6 stacked in that order from the lower side of the figure. The solid electrolyte of the six layers is densely airtight. The sensor element 101 is manufactured by stacking, for example, ceramic green sheets that have been processed according to the respective layers and provided with the respective circuit patterns by printing, and sintering the stack into one body.

In the sensor element 101, at one end thereof, a gas inlet 10, a first diffusion controlling portion 11, a buffering space 12, a second diffusion controlling portion 13, a first internal void space 20, a third diffusion controlling portion 30, and a second internal void space 40 are formed so as to communicate one after another in that order between the lower surface of the second solid electrolyte layer 6 and the upper surface of the first solid electrolyte layer 4.

The gas inlet 10, the buffering space 12, the first internal void space 20, and the second internal void space 40 are each a space in the sensor element 101 formed by boring the spacer 5 in such a manner that the upper side is defined by the lower surface of the second solid electrolyte layer 6, the lower side is defined by the upper surface of the first solid electrolyte layer 4, and the side walls are defined by the side surfaces of the spacer 5.

The first diffusion controlling portion 11, the second diffusion controlling portion 13, and the third diffusion controlling portion 30 are each provided with two laterally long slits therein (whose opening has a longitudinal direction perpendicular to the figure). The portion from the gas inlet 10 to the second internal void space 40 may be referred to as a gas delivering section.

At a position more distant from the end side than the gas delivering section, a reference gas introducing space 43 is formed between the upper surface of the third substrate 3 and the lower surface of the spacer 5 in such a manner that the side wall is defined by a side surface of the first solid electrolyte layer 4. Into the reference gas introducing space 43, for example, air is introduced as a reference gas for NOx concentration measurement.

An air introducing layer 48 is a porous layer made of a porous ceramic, and to which a reference gas is introduced through the reference gas introducing space 43. Also, the air introducing layer 48 is disposed so as to cover a reference electrode 42.

The reference electrode 42 is disposed between the upper surface of the third substrate 3 and the first solid electrolyte layer 4, and is provided therearound with the air introducing layer 48 communicating with the reference gas introducing space 43. The reference electrode 42 is used for measuring the oxygen concentration (oxygen partial pressure) in the first internal void space 20 and the second internal void space 40, as will be described later.

The gas inlet 10 in the gas delivering section is open to an external space, and through which a measurement-object gas is introduced into the sensor element 101 from the external space. The first diffusion controlling portion 11 gives a predetermined diffusion resistance to the measurement-object gas that has been introduced through the gas inlet 10. The buffering space 12 is intended to deliver the measurement-object gas introduced through the first diffusion controlling portion 11 to the second diffusion controlling portion 13. The second diffusion controlling portion 13 gives a predetermined diffusion resistance to the measurement-object gas that is being introduced to the first internal void space 20 through the buffering space 12. When a measurement-object gas is delivered to the first internal void space 20 from the outside of the sensor element 101, the measurement-object gas rapidly taken into the sensor element 101 through the gas inlet 10 by pressure fluctuation of the measurement-object gas (for the case of measuring automotive exhaust gas, pulsation of exhaust gas pressure) in the external space is passed through the first diffusion controlling portion 11, the buffering space 12, and the second diffusion controlling portion 13 to cancel the fluctuation in concentration of the measurement-object gas before being delivered to the first internal void space 20, instead of being directly delivered to the first internal void space 20, and is then delivered to the first internal void space 20. Thus, the fluctuation in concentration of the measurement-object gas delivered to the first internal void space 20 is substantially negligible. The first internal void space 20 is intended to control the oxygen partial pressure of the measurement-object gas delivered through the second diffusion controlling portion 13. The oxygen partial pressure is controlled by the operation of a main pump cell 21.

The main pump cell 21 is an electrochemical pump cell including an inner pump electrode 22 having a ceiling electrode portion 22a disposed over substantially the entire lower surface of the portion of the second solid electrolyte layer 6 opposing the first internal void space 20; an outer pump electrode 23 disposed so as to be exposed to the external space in the region of the upper surface of the second solid electrolyte layer 6 corresponding to the ceiling electrode portion 22a; and the second solid electrolyte layer 6 between the inner and the outer pump electrode.

The inner pump electrode 22 is formed so as to be across the upper and the lower solid electrolyte layer (the second solid electrolyte layer 6 and the first solid electrolyte layer 4) defining the first internal void space 20, and the spacer layer 5 defining the side walls. More specifically, the ceiling electrode portion 22a is formed on the lower surface of the second solid electrolyte layer 6 defining the ceiling of the first internal void space 20; a bottom electrode portion 22b is formed on the upper surface of the first solid electrolyte layer 4 defining the bottom of the first internal void space 20; and side electrode portions (not shown) are formed on the side wall surfaces (inner surfaces) of the spacer layer 5 defining the side walls of the first internal void space 20 so as to connect the ceiling electrode portion 22a and the bottom electrode portion 22b. Thus, the inner pump electrode 22 is in the form of a tunnel.

The inner pump electrode 22 and the outer pump electrode 23 are porous cermet electrodes (for example, cermet electrodes of Pt containing 1% of Au and $ZrO_2$). The inner pump electrode 22, which comes in contact with the measurement-object gas, is made of a material whose ability to reduce the NOx in the measurement-object gas has been weakened.

The main pump cell 21 is configured so that the oxygen in the first internal void space 20 can be pumped out to the external space or external oxygen can be pumped into the first internal void space 20 by applying a desired pump voltage Vp0 between the inner pump electrode 22 and the outer pump electrode 23 to pass a positive or negative pump current Ip0 between the inner pump electrode 22 and the outer pump electrode 23.

In addition, in order to detect the oxygen concentration (oxygen partial pressure) in the atmosphere in the first internal void space 20, the inner pump electrode 22, the second solid electrolyte layer 6, the spacer layer 5, the first solid electrolyte layer 4, the third substrate layer 3, and the reference electrode 42 constitute an electrochemical sensor cell, that is, a main pump controlling oxygen partial pressure detecting sensor cell 80.

By measuring the electromotive force V0 of the main pump controlling oxygen partial pressure detecting sensor cell 80, the oxygen concentration (oxygen partial pressure) in the first internal void space 20 can be known. Furthermore, the pump current Ip0 is controlled by feedback-controlling the pump voltage Vp0 of a variable power supply 24 so that the electromotive force V0 can be constant. Thus, the oxygen concentration in the first internal void space 20 is kept constant at a specific value.

The third diffusion controlling portion 30 gives a predetermined diffusion resistance to the measurement-object gas in which the oxygen concentration (oxygen partial pressure) has been controlled in the first internal void space 20 by the operation of the main pump cell 21 and delivers the measurement-object gas to the second internal void space 40.

The second internal void space 40 is formed as a space in which a process for measuring the nitrogen oxide (NOx) concentration in the measurement-object gas delivered through the third diffusion controlling portion 30 is performed. NOx concentration is measured mainly in the second internal void space 40 in which the oxygen concentration is controlled with an auxiliary pump cell 50, and, in addition, by the operation of a measurement pump cell 41.

The second internal void space 40 further controls, with the auxiliary pump cell 50, the oxygen partial pressure in the measurement-object gas that has been subjected to control of the oxygen concentration (oxygen partial pressure) in advance in the first internal void space 20 and then delivered through the third diffusion controlling portion 30. Thus, the oxygen concentration in the second internal void space 40 is precisely kept constant, and accordingly, the gas sensor 100 is allowed to highly precisely measure NOx concentration.

The auxiliary pump cell 50 is an auxiliary electrochemical pump cell including an auxiliary pump electrode 51 having a ceiling electrode portion 51a disposed over substantially the entire lower surface of the second solid electrolyte layer 6 that feces the second internal void space 40; the outer pump electrode 23 (an appropriate electrode outside the sensor element 101 suffices without being limited to the outer pump electrode 23); and the second solid electrolyte layer 6.

The auxiliary pump cell 51 is disposed in the second internal void space 40 at a tunnel shaped structure, in the same manner as the inner pump electrode 22 disposed in the first internal void space 20. More specifically, the ceiling electrode portion 51a is formed on the portion of the second solid electrolyte layer 6 defining the ceiling of the second internal void space 40; a bottom electrode portion 51b is formed on the portion of the first solid electrolyte layer 4 defining the bottom of the second internal void space 40; and side electrode portion (not shown) connecting the ceiling electrode portion 51a and the bottom electrode portion 51b are formed on the side wall surfaces of the spacer layer 5 defining the side walls of the second internal void space 20. As with the inner pump electrode 22, the auxiliary pump electrode 51 is made of a material whose ability to reduce the NOx in the measurement-object gas has been weakened.

The auxiliary pump cell 50 is configured so that the oxygen in the atmosphere in the second internal void space 40 can be pumped out to the external space or external oxygen can be pumped into the second internal void space 40 by applying a desired pump voltage Vp1 between the auxiliary pump electrode 51 and the outer pump electrode 23.

In addition, in order to control the oxygen partial pressure in the atmosphere in the second internal void space 40, the auxiliary pump electrode 51, the reference electrode 42, the second solid electrolyte layer 6, the spacer layer 5, the first solid electrolyte layer 4, and the third substrate layer 3 constitute an electrochemical sensor cell, that is, an auxiliary pump controlling oxygen partial pressure detecting sensor cell 81.

The pumping of the auxiliary pump cell 50 is operated by a variable power supply 52 whose voltage is controlled according to the electromotive force V1 detected by the auxiliary pump controlling oxygen partial pressure detecting sensor cell 81. Thus, the oxygen partial pressure in the atmosphere in the second internal void space 40 is controlled to be a low partial pressure that does not substantially affect NOx measurement.

In addition, pump current Ip1 is used for controlling the electromotive force of the main pump controlling oxygen partial pressure detecting sensor cell 80. More specifically, a pump current Ip1 is input as a control signal to the main pump controlling oxygen partial pressure detecting sensor cell 80 to control the electromotive force V0 of the sensor cell 80, thereby controlling the gradient of the oxygen partial pressure in the measurement-object gas that is being delivered to the second internal void space 40 through the third diffusion controlling portion 30 to be always constant. In use as a NOx sensor, the oxygen concentration in the second internal void space 40 is about 0.001 ppm and is thus kept constant by the operation of the main pump cell 21 and the auxiliary pump cell 50.

The measurement pump cell 41 measures the NOx concentration in the measurement-object gas in the second internal void space 40. The measurement pump cell 41 is an electrochemical pump cell including a measurement electrode 44 disposed on the upper surface of the first solid electrolyte layer 4 that faces the second internal void space 40, apart from the third diffusion controlling portion 30; the outer pump electrode 23; the second solid electrolyte layer 6; the spacer electrode 5; and the first solid electrolyte layer 4.

The measurement electrode 44 is a porous cermet electrode. The measurement electrode 44 functions also as a NOx reducing catalyst that reduces the NOx in the atmosphere in the second internal void space 40. The measurement electrode 44 is covered with a fourth diffusion controlling portion 45.

The fourth diffusion controlling portion 45 is a film made of a porous ceramic. The fourth diffusion controlling portion 45 not only functions to restrict the amount of NOx flowing into the measurement electrode 44, but also functions as a protective film of the measurement electrode 44. The measurement pump cell 41 pumps out oxygen produced by decomposition of the nitrogen oxides in the atmosphere around the measurement electrode 44 and detects the amount of the oxygen as pump current Ip2.

In addition, in order to detect the oxygen partial pressure in the atmosphere around the measurement electrode 44, the first solid electrolyte layer 4, the third substrate layer 3, the measurement electrode 44, and the reference electrode 42 constitute an electrochemical sensor cell, that is, a measurement pump controlling oxygen partial pressure detecting sensor cell 82. A variable power supply 46 is controlled according to the electromotive force V2 detected by the measurement pump controlling oxygen partial pressure detecting sensor cell 82.

The measurement-object gas delivered to the second internal void space 40 will reach the measurement electrode 44 through the fourth diffusion controlling portion 45 with an oxygen partial pressure controlled. The nitrogen oxide in the measurement-object gas around the measurement electrode 44 is reduced ($2NO \rightarrow N_2+O_2$) to produce oxygen. The oxygen thus produced will be pumped by the measurement pump cell 41. At this time, the voltage Vp2 of the variable power supply 46 is controlled so that the electromotive force V2 detected by the measurement pump controlling oxygen partial pressure detecting sensor cell 82 can be constant. Since the amount of oxygen produced around the measurement electrode 44 is proportional to the nitrogen oxide concentration in the measurement-object gas, the nitrogen oxide concentration in the measurement-object gas is calculated using the pump current Ip2 of the measurement pump cell 41.

Alternatively, by combining the measurement electrode 44, the first solid electrolyte layer 4, the third substrate layer 3, and the reference electrode 42 to constitute an oxygen partial pressure detecting mechanism as an electromechanical sensor cell, the electromotive force generated according to the difference between the amount of oxygen produced by reduction of the NOx in the atmosphere around the measurement electrode 44 and the amount of oxygen contained in the reference air can be detected, and thus the NOx concentration in the measurement-object gas can be determined from this electromotive force.

The electrochemical sensor cell 83 is made up of the second solid electrolyte layer 6, the spacer layer 5, the first solid electrolyte layer 4, the third substrate layer 3, the outer pump electrode 23, and the reference electrode 42. The oxygen partial pressure in the measurement-object gas outside the sensor can be determined from the electromotive force Vref generated in this sensor cell 83.

In the gas sensor 100 having the above-described structure, the measurement pump cell 41 receives a measurement-object gas in which the oxygen partial pressure is kept low and constant (to the extent that NOx measurement is substantially not affected) by the operation of the main pump cell 21 and the auxiliary pump cell 50. Thus, the NOx concentration in the measurement-object gas can be known according to the pump current Ip2 caused by the operation of the measurement pump cell 41 to pump out oxygen produced by reduction of NOx substantially in proportion to the NOx concentration in the measurement-object gas.

Furthermore, the sensor element 101 includes a heater section 70 adapted to heat the sensor element 101 and keep the sensor element 101 warm so as to increase the oxygen ion conductivity of the solid electrolyte. The heater section 70 includes a heater connector electrode 71, a heater 72, a portion defining a through-hole 73, a heater insulating layer 74, and a portion defining a pressure release hole 75. The heater section 70 also includes the first substrate layer 1, the second substrate layer 2, and the third substrate layer 3, each made of a ceramic. The heater section 70 is structured as a ceramic heater including the heater 72, and the second and the third substrate layer 2 and 3 surrounding the heater 72. The heater 72 includes a heating section 76 and a lead section 79, as shown in FIG. 2.

The heater connector electrode 71 is in contact with the lower surface of the first substrate layer 1. By connecting the heater connector electrode 71 to an external power source, electricity is supplied from the outside to the heater section 70.

The heating section 76 of the heater 72 is an electric resistor disposed between the second substrate layer 2 and the third substrate layer 3 in contact therewith. The lead section 79 of the heater 72 is connected to the heater connector electrode 71 through the through-hole 73. When electricity is supplied through the heater connector electrode 71 from the outside, the heating section 76 heats to heat the solid electrolyte of the sensor element 101 and keep the solid electrolyte warm.

The heating section 76 of the heater 72 is embedded under the entire region from the first internal void space 20 to the second internal void space 40 so as to control the entirety of the sensor element 101 to a temperature at which the solid electrolyte is activated.

The heater insulating layer 74 is an insulating layer formed of an insulating material such as alumina over the upper and the lower surface of the heater 72. The heater insulating layer 74 is formed to provide electrical insulation between the second substrate layer 2 and the heater 72 and electrical insulation between the third substrate layer 3 and the heater 72.

The pressure release hole 75 passes through the third substrate layer 3 and communicates with the reference gas introducing space 43 and is intended to alleviate internal pressure increase with increasing temperature in the heater insulating layer 74.

The heating section 76 and the lead section 79 of the heater 72 will now be described in detail. The heating section 76 is a resistance heating element and has a shape of a one-stroke strip connected to the lead section 79, as shown in FIG. 2. The heating section 76 includes a plurality (three, in the present embodiment) of curved portions 77 and a plurality (four, in the present embodiment) of straight portions 78. The curved portions 77 and the straight portions 78 are electrically connected in series. The heating section 76 is bilaterally symmetrical.

The straight portions 78 are arranged at regular intervals in the short-length direction (left-right direction) of the sensor element 101. Each of the straight portions 78 extends along the longitudinal direction (front-rear direction) of the sensor element 101. In the present embodiment, the straight portions 78 are arranged in such a manner that the length direction thereof is parallel to the front-rear direction. The rear end of the leftmost one of the straight portions 78 is connected to a first lead 79a that is a positive lead. The rear end of the rightmost one of the straight portions 78 is connected to a second lead 79b that is a negative lead.

Each curved portion 77 connects a pair of the straight portions 78 adjacent to each other in the left-right direction. The curved portions 77 include non-lead side curved portions 77a, each connecting the front ends (far from the lead section 79) of a pair of the adjacent straight portions 78, and at least one lead side curved portion 77b connecting the rear ends (closer to the lead section 79) of a pair of the adjacent straight portions 78. In the present embodiment, the curved portions 77 include two non-lead side curved portions 77a and one lead side curved portion 77b. Since the number of lead side curved portions 77b is one, the lead side curved portion 77b is the closest to the lead section 79 of the at least one lead side curved portion and is, in addition, the closest lead side curved portion to the first lead 79a (positive lead). The lead side curved portion 77b and the first lead 79a are closest between points P1 and P2 in FIG. 2. The lead side curved portion 77b and the second lead 79b are also closest between points P3 and P4. The distance between points P1 and P2 will be referred to as distance L1, and the distance between points P3 and P4 will be referred to as distance L2. Distance L1 is equal to distance L2. Each of the plurality of curved portions 77 is bent to form a curve and in the shape of the arc of a semicircle. The curved portions 77 may have a linearly bent shape.

In the present embodiment, the heating section 76 is made of a cermet containing a noble metal and a ceramic (for example, platinum (Pt) and alumina ($Al_2O_3$)). The material of the heating section 76 may be an electroconductive material such as a noble metal without being limited to cermet. Examples of the noble metal used in the heating section 76 include at least one of platinum, rhodium (Rh), gold (Au), and palladium (Pd), or an alloy of these noble metals.

The lead side curved portion 77b that is the closest lead side curved portion to the lead section and to the positive lead has a lower resistance per unit length than the straight portions 78 at one or more temperatures in the range of 700° C. to 900° C. to which the heating section 76 can be heated. In other words, the ratio R1/R2 of unit resistance R1 [$\mu\Omega$/mm] that is the resistance per unit length of the lead side curved portion 77b to unit resistance R2 [$\mu\Omega$/mm] that is the resistance per unit length of the straight portions 78 is less than 1 at one or more temperatures in that temperature range. Thus, the lead side curved portion 77b has a lower heating density (quantity of heat generation per unit length) than the straight portions 78 at one or more temperatures in the range of 700° C. to 900° C., and accordingly, the temperature increase of this curved portion is suppressed. By controlling the unit resistance ratio R1/R2 to less than 1, the temperature increase of the lead side curved portion 77b can be suppressed, and the degradation of the heater 72 resulting from migration (that will be described in detail later) can be reduced compared to the case where the unit resistance ratio R1/R2 is 1 or more.

The length directions of the lead side curved portion 77b and the straight portions 78 correspond to the axis directions of the lead side curved portion 77b and the straight portions 78, respectively; hence, current flows along these directions. Unit resistance R1 is defined by the average of resistances per unit length of the lead side curved portion 77b. Similarly, unit resistance R2 is defined by the average of resistances per unit length of the plurality of straight portions 78. Therefore, even if a portion of the lead side curved portion 77b has a higher resistance per unit length than the straight portions 78, the resistance per unit length of the lead side curved portion 77b as a whole is lower than that of the straight portions 78. It is however preferable that at least the closest portion (at points P1 and P3) of the lead side curved portion 77b to the lead section 79 have a lower resistance per unit length than unit resistance R2. More preferably, the resistance per unit length of any portion of the lead side curved portion 77b is lower than unit resistance R2. In the heating section 76, preferably, the unit resistance ratio R1/R2 is less than 1 at any temperature in the above temperature range. In the heating section 76, more preferably, the unit resistance ratio R1/R2 is 0.87 or less, more preferably 0.80 or less, at one or more temperatures in the above temperature range. The unit resistance ratio R1/R2 may be 0.5 or more at any temperature in the above temperature range.

In the present embodiment, the lead side curved portion 77b and the straight portions 78 are made of the same material (cermet containing platinum, as described above), and the area S1 [mm$^2$] of the cross section of the lead side curved portion 77b taken in the direction perpendicular to the length direction thereof is larger than the area S2 [mm$^2$] of the cross section of the straight portions 78 taken in the direction perpendicular to the length direction thereof. Hence, the heating section 76 has a cross-sectional area ratio S2/S1 of less than 1. In this instance, the unit resistance ratio R1/R2 is less than 1 at any temperature in the range of 700° C. to 900° C. Preferably, the cross-sectional area ratio S2/S1 is 0.87 or less, more preferably 0.80 or less. The cross-sectional area ratio S2/S1 may be controlled, for example, by at least either the operations of controlling the width W1 of the lead side curved portion 77b to be larger than the width W2 of the straight portions 78, or the operation of controlling the thickness D1 of the lead side curved portion 77b to be larger than the thickness D2 of the straight portions 78. For example, in the case of width W1>width W2, any relationship of thickness D1<thickness D2, thickness D1=thickness D2, and thickness D1>thickness D2 may hold true, as long as the cross-sectional area ratio S2/S1 is less than 1. Similarly, in the case of thickness D1>thickness D2, any relationship of width W1<width W2, width W1=width W2, and width W1>width W2 may hold true, as long as the cross-sectional area ratio S2/S1 is less than 1. Cross-sectional areas S1 and S2 are defined by the averages thereof of the lead side curved portion 77b and the straight portions 78, respectively, as with unit resistances R1 and R2. It is also preferable that the cross section of the lead side curved portion 77b (taken in the direction perpendicular to the length direction thereof) at least at the closest point (at points P1 and P3) thereof to the lead section 79 have a larger area than cross-sectional area S2. In the present embodiment, the straight portions 78 have the same cross-sectional area (=cross-sectional area S2) at any position. The two non-lead side curved portions 77a have the same cross-sectional area as the straight portions 78. The cross-sectional area of the lead side curved portion 77b is the same as the cross-sectional area of the straight portions 78 at the joint with the straight portions 78, and is gradually increased with increasing distance from the straight portion 78. Hence, each of the at least one lead side curved portion 77b has a cross section varying so as to be largest at the center in the left-right direction (cross-section passing through the point most protruding to the rear side). The cross-sectional area ratio S2/S1 may be 0.5 or more. Widths W1 and W2 may be in the range of 0.05 mm to 1.5 mm. Thicknesses D1 and D2 may be in the range of 0.003 mm to 0.1 mm.

The lead section 79 includes the first lead 79a located to the rear left of the heating section 76, and the second lead 79b located to the rear right of the heating section 76. The first and the second lead 79a and 79b are used for supplying electricity to the heating section 76 and are connected to the heater connector electrode 71. The first lead 79a is a positive lead, and the second lead 79b is a negative lead. By applying a voltage between the first and the second lead 79a and 79b, a current flows to the heating section 76, and thus the heating section 76 heats. The lead section 79, which is an electric conductor, has a lower resistance per unit length than the heating section 76. Unlike the heating section 76, the lead section 79 therefore hardly heats during power supply. For example, the lead section 79 may be made of a material having a lower volume resistivity than the material of the heating section 76 or have a larger cross-sectional area than the heating section 76 so as to have a lower resistance per unit length. In the present embodiment, the volume resistivity of the lead section 79 is reduced by adding a noble metal with a higher content than that in the heating section 76, and the cross-sectional area of the lead section 79 is made larger than that of the heating section 76 by controlling the width of the lead section 79 to be larger than that of the heating section 76. The width of the lead section 79 in the left-right direction is substantially the same as the forward straight portion 78 at the joint therebetween and is increased toward the rear side.

A method for manufacturing the gas sensor 100 having the above-described structure will now be described. First, six ceramic green sheets containing an oxygen ion conductive solid electrolyte, such as zirconia, as a ceramic component, are prepared. In these green sheets, alignment holes used for printing or stacking, through-holes, and the like have been formed in advance. The green sheet for the spacer layer 5 is provided therein with a space for the gas delivering section that has been formed by punching. Then, different patterns are formed respectively on the ceramic green sheets for the first substrate layer 1, the second substrate layer 2, the third substrate layer 3, the first solid electrolyte layer 4, the spacer layer 5, and the second solid electrolyte layer 6 by pattern printing and drying. More specifically, the patterns to be formed are for, for example, the above-described electrodes, lead wires connected to the electrodes, the air introducing layer 48, the heater 72, and the like. For the pattern printing, a pattern forming paste prepared according to the characteristics required for the intended pattern is applied onto a green sheet by a known screen printing technique. The pattern forming paste for the heater 72 is a mixture containing the raw material (for example, a noble metal and ceramic particles) for the heater 72, an organic binder, and an organic solvent.

The pattern for the heater 72 is formed so that the unit resistance ratio R1/R2 will be less than 1, that is, so that the cross-sectional area ratio S2/S1 will be less than 1. For example, for satisfying the relationship width W1>width W2, a mask enabling such a pattern to be formed is used. For satisfying the relationship thickness D1>thickness D2, for example, the pattern forming paste for the lead side curved portion 77b is prepared so as to have a higher viscosity than the pattern forming paste for the straight portions 78, or the number of printing operations for forming the pattern for the lead side curved portion 77b is increased.

After the various patterns are formed, the green sheets are dried. The drying process is performed by using a known drying means. After the pattern printing and drying are finished, the green sheets are subjected to printing of an adhesive paste for stacking and bonding the green sheets, followed by drying. Then, the resulting green sheets are stacked in a predetermined order with the holes in the sheets aligned. The stack is subjected to pressure bonding for forming a multilayer body by being heated to a predetermined temperature under a predetermined pressure. The resulting multilayer body includes a plurality of sensor elements 101. The multilayer body is cut into pieces having a size corresponding to the sensor element 101. The pieces of the multilayer body are sintered at a predetermined temperature to yield sensor elements 101.

The sensor element 101 thus produced is incorporated in a sensor assembly, and a protective cover, for example, is attached to the assembly. Thus, a gas sensor 100 is completed. The process for manufacturing a gas sensor has been known except for the technique of setting the unit resistance ratio R1/R2 to less than 1, and is disclosed in, for example, International Publication No. 2013/005491.

For use of the resulting gas sensor 100, the heater 72 is connected to a power source (for example, the alternator of an automobile) through the heater connector electrode 71, and a direct voltage (for example, 12 V to 14 V) is applied between the first lead 79a and the second lead 79b. The applied voltage causes a current to flow in the heating section 76. The heating section 76 thus heats. Thus, the entirety of the sensor element 101 is controlled to a temperature (for example, 700° C. to 900° C.) at which the solid electrolyte (of layers 1 to 6) is activated. At this time, in portions of the heater 72 (the heating section 76 and the lead section 79) having a higher potential gradient (=potential difference/distance between surfaces) between the surfaces, impurities (for example, oxides of alkali metal or alkaline-earth metal) in the heater 72 or the heater insulating layer 74 can be ionized. Ions thus produced include cations such as sodium ion ($Na^+$), calcium ion ($Ca^{2+}$), and magnesium ion ($Mg^{2+}$), and anions such as oxide ion ($O^{2-}$). If these ions are produced, cations are attracted to the low potential side, and anions are attracted to the high potential side. Thus ions move in the heater insulating layer 74 in some cases. This phenomenon is called migration. Ions that have migrated to a portion of the heater 72 react with a constituent in the portion (for example, react with a noble metal in the heater 72), thus degrading the heater 72 in such a manner that a line of the pattern is thinned or broken. In addition, ionization of impurities as described above is more likely to occur as temperature increases. In the present embodiment, the lead side curved portion 77b is close to the lead section 79, and accordingly, the potential gradient between the lead side curve portion 77b and the lead section 79 is higher than that between the other portions of the heating section 76 and the lead section 79. More specifically, the region between points P1 and P2 has a short distance L1 and has a potential difference about half that of the region between the first and the second lead 79a and 79b (for example, 12 V to 14 V), accordingly having a relatively high potential gradient. Similarly, the region between points P3 and P4 has a relatively high potential gradient. Accordingly, migration is likely to occur between the lead side curved portion 77b and the first lead 79a. Thus, the lead side curved portion 77b is likely to be degraded by migration of cations to point P1, and the first lead 79a is likely to be degraded by migration of anions to point P2. Migration is also likely to occur between the lead side curved portion 77b and the second lead 79b. Thus, the second lead 79b is likely to be degraded by migration of cations to point P4, and the lead side curved portion 77b is likely to be degraded by migration of anions to point P3. In the present embodiment, however, the unit resistance ratio R1/R2 is set to be less than 1 at one or more temperatures in the range of 700° C. to 900° C. Thus, the lead side curved portion 77b has a lower heating density than the straight portions 78 at one or more temperatures in the range of 700° C. to 900° C., and accordingly, the temperature increase of the lead side curved portion 77b is suppressed. Since the temperature increase of the lead side curved portion 77b, in which migration is less likely to occur, and of the surroundings thereof is suppressed, ionization as described above is prevented, and migration is prevented. Thus, the lead side curved portion 77b and the first and the second lead 79a and 79b can be prevented from being degraded by migration. Thus, the degradation of the heater 72 is reduced, so that the lifetime of the heater 72 is extended.

The relationship between the components of the present embodiment and the components of the present invention will now be clearly described. The heater section 70 of the present embodiment corresponds to the ceramic heater of the present invention; a stack of the first substrate layer 1, the second substrate layer 2, and the third substrate layer 3 corresponds to the plate-like ceramic body; the heater 72 corresponds to the heating element; the straight portion 78 corresponds to the straight portion; and the lead side curved portion 77b corresponds to the lead side curved portion. The closest lead side curved portion 77b to the lead section corresponds to the closest to the lead section of the at least one lead side curved portion of the first ceramic heater of the present invention, and the closest lead side curved portion 77b to the positive lead corresponds to the closest to the positive lead of the at least one lead side curved portion of the second ceramic heater.

According to the gas sensor 100 of the present embodiment, the heater section 70 includes a plate-like ceramic body (the first substrate layer 1, the second substrate layer 2, and the third substrate layer 3) having a longitudinal direction and a short-length direction, and a heater 72 disposed within the plate-like ceramic body and including a lead section 79 and a heating section 76 connected to the lead section 79. The heating section 76 includes a straight portion 78 extending along the longitudinal direction, and a lead side curved portion 77b connected to one of the ends of the straight portion 78 closer to the lead section 79. The lead side curved portion 77b that is the closest lead side curved portion to the lead section and to the positive lead has a lower resistance per unit length than the straight portion 78 at one or more temperatures in the range of 700° C. to 900° C. Accordingly, the lead side curved portion 77b has a lower heating density than the straight portion 78 at one or more temperatures in the range of 700° C. to 900° C., and thus the temperature increase of the lead side curved portion 77b is suppressed. Thus, at least either the lead side curved portion 77b or the lead section 79 can be prevented from being degraded by migration, and the degradation of the heater 72 is reduced. Apart from the degradation resulting from migration, the heater 72 is more likely to be degraded by oxidation (for example, oxidation of Pt that is a noble metal in the heating section 76) with increasing temperature. Since the temperature increase of the lead side curved portion 77b is suppressed, the lead side curved portion 77b is prevented from being degraded by oxidation, as well from degraded by migration.

In addition, by setting the unit resistance ratio R1/R2 to be 0.87 or less at one or more temperatures in the above temperature range, the degradation of the heater 72 resulting from migration is reduced more effectively. Furthermore, by setting the unit resistance ratio R1/R2 to be 0.80 or less at one or more temperatures in the above temperature range, the degradation of the heater 72 resulting from migration is reduced still more effectively. Since the cross-section of the lead side curved portion 77b taken in the direction perpendicular to the length direction thereof has a larger area than that of the straight portions 78, the resistance per unit length (unit resistance R1) of the lead side curved portion 77b tends to be lower than the unit resistance R2 of the straight portions 78. Also, by setting the cross-sectional area of the lead side curved portion 77b to be larger than that of the straight portions 78, the amount per unit length of noble metal in the lead side curved portion 77b is larger than that in the straight portions 78. Even if degradation resulting from migration occurs in the lead side curved portion 77b, therefore, the lead side curved portion 77b will take a long time to be entirely degraded. Thus, adverse effects of such degradation is unlikely to be produced and, for example, disconnection resulting from degradation is unlikely to occur. Thus, the lifetime of the lead side curved portion 77b is extended. When the cross-sectional area ratio S2/S1 is 0.87 or less, the unit resistance ratio R1/R2 tends to be 0.87 or less at one or more temperatures in the above temperature range. Also, when the cross-sectional area ratio S2/S1 is 0.80 or less, the unit resistance ratio R1/R2 tends to be 0.80 or less at one or more temperatures in the above temperature range.

Furthermore, the heating section 76 may have four or more straight portions 78 arranged along the short-length direction (left-right direction) of the plate-like ceramic body. In this structure, the at least one lead side curved portion 77b connects a pair of the straight portions 78 adjacent to each other in the short-length direction at one of the ends of each adjacent straight portion closer to the lead section 79, and the heating section 76 has a plurality of non-lead side curved portions 77a, each connecting a pair of the straight portions 78 adjacent to each other in the short-length direction at one of the ends of each adjacent straight portion far from the lead section 79. The sensor element 101 includes the heater section 70 and detects the concentration of a specific gas in a measurement-object gas. The gas sensor 100 includes the sensor element 101.

The present invention is not limited to the above-described embodiment, and it should be appreciated that various embodiments can be applied to the invention within the technical scope of the invention.

For example, while the cross-sectional area ratio S2/S1 is 1 or less in the above-described embodiment, it is not limited thereto as long as the unit resistance ratio R1/R2 is less than 1 at one or more temperatures in the range of 700° C. to 900° C. For example, the lead side curved portion 77b may have a lower volume resistivity than the straight portions 78 at one or more temperatures in that temperature range. Hence, the volume resistivity ratio $\rho1/\rho2$ of the volume resistivity $\rho1$ [$\mu\Omega\cdot cm$] of the lead side curved portion 77b to the volume resistivity $\rho2$ [$\mu\Omega\cdot cm$] of the straight portions 78 may be less than 1 at one or more temperatures in the above temperature range. The unit resistance ratio R1/R2 thus can be set to be less than 1 at one or more temperatures in the above temperature range. Consequently, the degradation of the heater 72 resulting from migration can be reduced. Preferably, the volume resistivity ratio $\rho1/\rho2$ is 0.87 or less, more preferably 0.80 or less, at one or more temperatures in the above temperature range. For example, by setting the noble metal (electroconductive material) content in the lead side curved portion 77b to be higher than that in the straight portions 78, volume resistivity $\rho1$ can be set to be lower than volume resistivity $\rho2$. Furthermore, by setting the noble metal content in the lead side curved portion 77b to be higher than that in the straight portions 78, the amount per unit length of noble metal in the lead side curved portion 77b can be set to be higher than that in the straight portions 78, as in the case of relatively increasing the cross-sectional area of the lead side curved portion 77b. When the amount per unit length of noble metal in the lead side curved portion 77b is relatively increased, adverse effects of degradation is unlikely to be produced. Thus, the lifetime of the lead side curved portion 77b is extended. Alternatively, by adding a noble metal (rhodium, gold, or the like) having a lower volume resistivity than platinum to the lead side curved portion 77b in addition to or instead of adding platinum while the straight portions 78 mainly contains platinum, volume resistivity $\rho1$ can be set to be lower than volume resistivity $\rho2$. In other words, the lead side curved portion 77b may contain a noble metal that is not contained in the straight portions 78 and has a lower volume resistivity than the noble metal contained in the straight portions 78. Alternatively, by adding to the lead side curved portion 77b a material whose resistance has a lower temperature coefficient (unit: [%/° C.]) than the noble metal mainly contained in the lead side curved portion 77b, with a higher proportion than in the straight portions 78, volume resistivity $\rho1$ can be set to be lower than volume resistivity $\rho2$ at one or more temperatures in the above temperature range. Examples of the material whose resistance has a low temperature coefficient include Nichrome (alloy containing nickel (Ni) and chromium (Cr)), Kanthal (registered trademark, alloy containing iron, chromium, and aluminum), and molybdenum disilicide ($MoSi_2$). Volume resistivities $\rho1$ and $\rho2$ are defined as the averages thereof in the lead side curved portion 77b and the straight portions 78, respectively, as with unit resistances R1 and R2. The volume resistivity ratio $\rho1/\rho2$ may be 0.5 or more at any temperature in the above temperature range.

It may be combined in the heater section 70 to set the cross-sectional area ratio S2/S1 to be less than 1 and to set the volume resistivity ratio $\rho1/\rho2$ to be less than 1. For example, the product (=unit resistance ratio R1/R2) of the cross-sectional area ratio S2/S1 and the volume resistivity ratio $\rho1/\rho2$ may be set to be less than 1, 0.87 or less, or 0.80 or less at one or more temperatures in the above temperature range. When the cross-sectional area ratio S2/S1 is less than 1, the lead side curved portion 77b and the straight portions 78 may be made of different materials.

Figure 3:
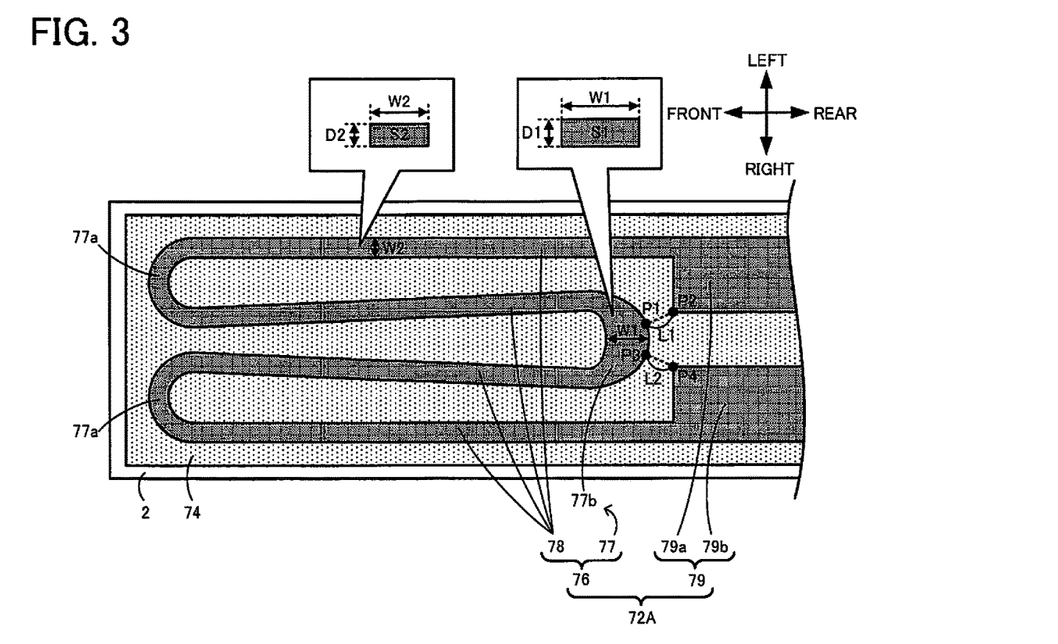
FIG. 3 is an explanatory view of a heater 72A according to a modification.

The shape (pattern) of the heater 72 in the heater section 70 is not limited to the above-described embodiment. The heating section 76 of the heater 72 includes the lead side curved portion 77b and the straight portions 78 and is otherwise not limited. The straight portions 78 are not necessarily parallel to each other as long as they extend along the longitudinal direction (front-rear direction) of the heater section 70. FIG. 3 is an illustrative representation of a heater 72A according to a modification. In this heater 72A, two of the four straight portions 78, located at the center in the left-right direction extend along the longitudinal direction, but are inclined with respect to the longitudinal direction. More specifically, the second straight portion 78 from the left is inclined to the left while extending to the rear side, and the second straight portion 78 from the right is inclined to the right while extending to the rear side. This shape enables the curved portions 77 to have a larger radius (radius of curvature) than that of the heater 72 shown in FIG. 2. In other words, the width of the heating section 76 in the left-right direction can be reduced without reducing the radius of curvature of the lead side curved portion 77b. Also, unlike the shape shown in FIG. 2, the joint of the lead section 79 with the forward straight portion 78 has a wider width than the straight portion 78. This lead section 79 may have the same shape as in FIG. 2, or the lead section 79 of the heater 72 shown in FIG. 2 may have the same shape as in FIG. 3. The heater 72A of this modification can produce the same effect as in the above-described embodiment. For example, by setting the unit resistance ratio R1/R2 to be less than 1 at one or more temperatures in the range of 700° C. to 900° C., the degradation of the heater 72 resulting from migration can be reduced.

While the above-described embodiment has been illustrated for the heating section 76 including three curved portions 77 and four straight portions 78, the heating section is not limited thereto as long as the heating section 77 includes at least one straight portion 78 and at least one lead side curved portion 77b connected to the straight portion 78. For example, the number of the curved portions 77 may be three or more, or one or two, and the number of the straight portions 78 may be four or more, or three or less. The number of the straight portions 78 may be an even number of four or more. While the above-described embodiment has been illustrated for the case of having two non-lead side curved portions 77a and one lead side curved portion 77b, the numbers of these curved portions may be varied according to the number of straight portions 78. For example, the number of the non-lead side curved portions 77a may be one or two or more, as long as the number of the lead-side curved portions 77b is one or more.

Figure 4:
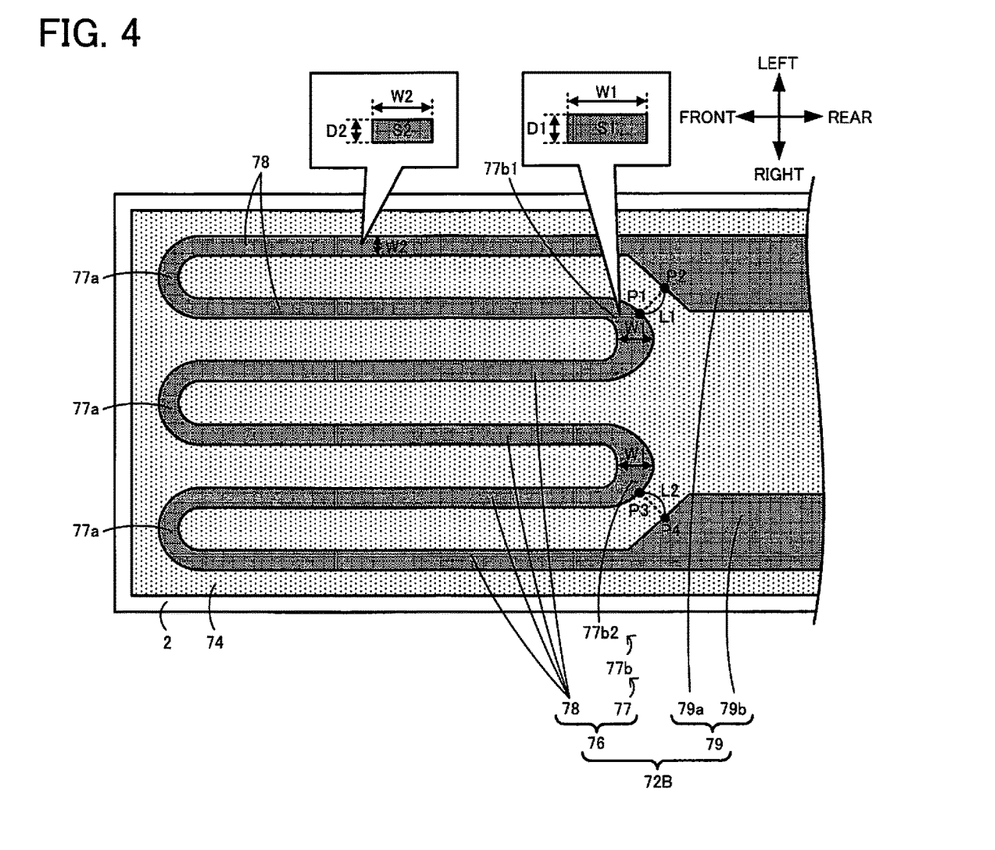
FIG. 4 is an explanatory view of a heater 72B according to a modification.

FIG. 4 is an illustrative representation of a heater 72B according to a modification in which the heating section 76 includes two lead side curved portions 77b. The heating section 76 of the heater 72B includes six straight portions 78 arranged in the short-length direction, three non-lead side curved portions 77a, and two lead side curved portions 77b (lead side curved portions 77b1 and 77b2). If distance L1 is equal to distance L2 in this heater 72B, both of the lead side curved portions 77b1 and 77b2 are the closest to the lead section of the lead side curved portions. In the case of distance L1<distance L2, the lead side curved portion 77b1 is the closest lead side curved portion; in the case of distance L1>distance L2, the lead side curved portion 77b2 is the closest lead side curved portion. The closest to the positive lead of the lead side curved portions is the lead side curved portion 77b1 irrespective of the lengths of distances L1 and L2. Thus, when the number of the lead side curved portions 77b is two or more, the closest lead side curved portion to the lead section and the closest lead-side curved portion to the positive lead may be different. In this case, at least either the closest lead side curved portion to the lead section or the closest lead side curved portion to the positive lead satisfies the unit resistance ratio R1/R2 of less than 1 at one or more temperatures in the above temperature range. Thus, the degradation of the heater 72 resulting from migration can be reduced as in the case of the above-described embodiment. More specifically, at least either the closest lead side curved portion to the lead section 79 or the lead section 79 can be prevented from being degraded as long as the unit resistance R1 of the closest lead side curved portion is lower than unit resistance R2. Also, at least either the closest lead side curved portion to the positive lead or the first lead 79a (positive lead) can be prevented from being degraded as long as the unit resistance R1 of the closest lead side curved portion to the positive lead is lower than unit resistance R2. In comparison between the lead section 79 and the lead side curved portion 77b, the lead side curved portion 77b, which is likely to have higher temperature, is more likely to be degraded than the lead section 79. If the cross section of the lead section 79 taken in the direction perpendicular to length direction thereof has a larger area than that of the lead side curved portion 77b, the lead section 79 will take a long time to be entirely degraded, and accordingly, the lead side curved portion 77b is more likely to be degraded. If the number of the lead side curved portions 77b is two or more, the unit resistance R1 that is the resistance per unit length of at least either the closest lead side curved portion to the positive lead or the closest to the negative lead of the two or more lead side curved portions 77b satisfies the unit resistance ratio R1/R2 of less than 1 at one or more temperatures in the above temperature range. Also, the unit resistance R1 that is the resistance per unit length of each of the closest lead side curved portion to the positive lead and the closest lead side curved portion to the negative lead may satisfy the unit resistance ratio R1/R2 of less than 1 at one or more temperatures in the above temperature range.

Figure 5:
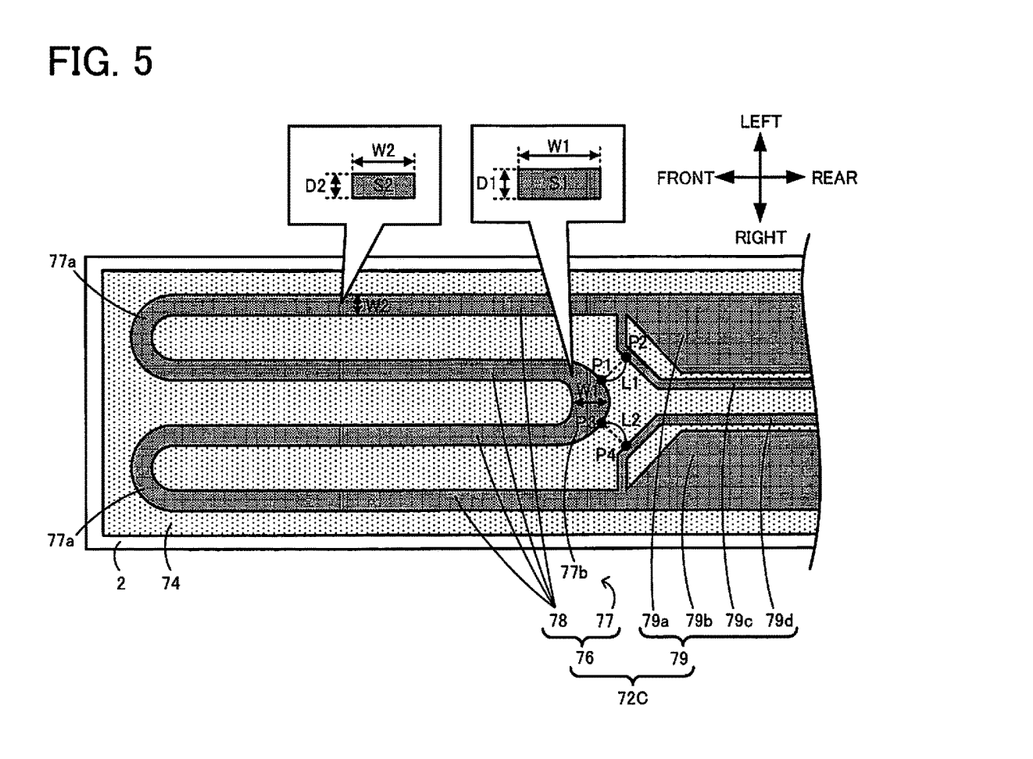
FIG. 5 is an explanatory view of a heater 72C according to a modification.

In the above-described embodiment, the lead section 79 includes the first and the second lead 79a and 79b for supplying electricity. In addition, the lead section 79 may further include any other lead, such as a lead used for measuring voltage. FIG. 5 is an illustrative representation of a heater 72C according to a modification in this case. In the heater 72C, the lead section 79 includes a third and a fourth lead 79c and 79d used for measuring voltage, in addition to the first and the second lead 79a and 79b for supplying electricity. The third lead 79c is connected to the joint between the first lead 79a and the corresponding straight portion 78 so as to be connected to the first read 79a in parallel. The fourth lead 79d is connected to the joint between the second lead 79b and the corresponding straight portion 78 so as to be connected to the second read 79b in parallel. In this heater 72C, the voltage between the third and the fourth lead 79c and 79d can be measured in a state where a voltage is applied between the first and the second lead 79a and 79b. Thus, the voltage between both ends of the heating section 76 can be accurately measured, eliminating an error resulting from the resistances of the first and the second lead 79a and 79b (what is called four-terminal method). In the heater 72C, the first and the third lead 79a and 79c correspond to the positive lead, and the second and the fourth lead 79b and 79d corresponds to the negative lead. In this heater 72C, the lead side curved portion 77b is close to the third and the fourth lead 79c and 79d. Accordingly, the potential gradient between the lead side curved portion 77b and the third lead 79c (for example, between points P1 and P2) and between the lead side curved portion 77b and the fourth lead 79d (for example, between points P3 and P4) tends to increase. Therefore, by setting the unit resistance R1 of the lead side curved portion 77b that is the closest to the lead section and to the positive lead of the at least one lead side curved portion to be lower than unit resistance R2, the degradation of the heater 72 resulting from migration can be reduced as in the case of the above-described embodiment. In the heater 72C shown in FIG. 5, the lead section 79 does not necessarily include the fourth lead 79d. In this instance, the voltage between the first and the second lead 79a and 79c (=voltage drop of the first lead 79a) is substantially equal to the voltage drop of the second lead 79b. Therefore, the voltage between both ends of the heating section 76 can be accurately obtained as the remainder of the subtraction of the voltage between the first and the third lead 79a and 79c from the voltage between the third and the second lead 79c and 79b. In the case of not including the fourth lead 79d, as well as in the above case, by setting the unit resistance R1 of the lead side curved portion 77b that is the closest to the lead section and to the positive lead of the at least one lead side curved portion to be lower than unit resistance R2, the degradation of the heater 72 resulting from migration can be reduced as in the case of the above-described embodiment.

While the above-described embodiment has been illustrated for the case in which the cross-sectional area of the lead side curved portion 77b increases as the distance from the straight portion 78 increases, it is not limited thereto. For example, the cross-sectional area of the lead side curved portion 77b may be the same (=cross-sectional area S1) at any point. In this instance, a step may be formed at the joint between the straight portion 78 and the lead side curved portion 77b. It is, however, preferable that there be no step in the heating section 76. For giving different cross-sectional areas to the lead side curved portion 77b and the straight portion 78, it is preferable to gradually vary the cross-sectional area of the lead side curved portion 77b, as shown in FIG. 2. Also, the straight portions 78 have the same cross-sectional area (=cross-sectional area S2) at any position. It is however not limited thereto. For example, the straight portions 78 may have a portion whose cross-sectional area gradually varies. If the heating section 76 includes a plurality of lead side curved portions 77b, at least one of the plurality of lead side curved portions 77b may have a different cross-sectional area from the other lead side curved portions 77b. The same applies to the case of a plurality of straight portions 78.

While the above-described embodiment has been illustrated for the case in which the two non-lead side curved portions 77a has the same cross-sectional area as the cross-sectional area of the straight portions 78, it is not limited thereto. The lead side curve portion 77b and the straight portions 78 satisfy the unit resistance ratio R1/R2 of less than 1 at one or more temperatures in the above temperature range and are otherwise not limited. For example, the cross-sectional area of the non-lead side curved portions 77a may be smaller than or larger than that of the straight portions 78. Similarly, the cross-sectional area of the non-lead side curved portions 77a may be smaller than, larger than, or the same as that of the lead side curve portion 77b.

While the above-describe embodiment has been illustrated for the heater 72 in the form of a strip, it is not limited thereto and may be in the form of a line (for example, having a circular or oval cross section).

While the above-described embodiment has been illustrated for the gas sensor 100 including the heater section 70, the present invention may be embodied as an independent sensor element 101, or an independent heater section 70, that is, an independent ceramic heater. While the heater section 70 described above includes the first substrate layer 1, the second substrate layer 2, and the third substrate layer 3, it is not limited thereto as long as it includes a plate-like ceramic body surrounding the heater 72. For example, the layer underlying the heater 72 may be defined by only a single layer, but not by the two layers of the first substrate layer 1 and the second substrate layer 2. While the heater section 70 described above includes the heater insulating layer 74, the heater insulating layer 74 may be omitted as long as the plate-like ceramic body (for example, the first substrate layer 1, the second substrate layer 2) surrounding the heater 72 is made of an insulating material (such as alumina ceramic). The sensor element 101 may have a length in the range of 25 mm to 100 mm in the front-rear direction, a width in the range of 2 mm to 10 mm in the left-right direction, and a thickness in the range of 0.5 mm to 5 mm in the vertical direction.

EXAMPLES

Examples in which sensor elements were specifically manufactured will now be described. Experimental Examples 2 to 9 and 11 to 18 correspond to Examples of the present invention, and Experiment Examples 1 and 10 correspond to Comparative Examples. It should be noted that the invention is not limited to the examples below.

Experimental Examples 1 to 9

Sensor elements 101 as shown in FIGS. 1 and 2 were prepared as Experimental Examples 1 to 9 in accordance with the method for manufacturing the gas sensor 100 of the above-described embodiment. Experimental Examples 1 to 9 had the same structure except that the cross-sectional area ratio S2/S1 was varied as shown in Table 1 by varying the width W1 of the lead side curved portion 77b. The sensor element 101 measured 67.5 mm in length in the front-rear direction, 4.25 mm in width in the left-right direction, and 1.45 mm in thickness in the vertical direction. In Experimental Example 1, the width W1 of the lead side curved portion 77b and the width W2 of the straight portions 78 were each 0.25 mm. Also, in Experimental Example 1, the thickness D1 of the lead side curved portion 77b and the thickness D2 of the straight portions 78 were each 0.01 mm. For producing the sensor element 101, ceramic green sheets were formed of a mixture of zirconia particles containing 4% by mole of yttria as a stabilizing agent, an organic binder, and an organic solvent by tape formation. The electroconductive paste for forming heating section 76 of the heater section 70 was prepared as below. A preliminary mixture was prepared by preliminarily mixing 4% by mass of alumina particles, 96% by mass of Pt, and a predetermined amount of acetone as a solvent. An organic binder liquid prepared by dissolving 20% by mass of polyvinyl butyral in 80% by mass of butyl carbitol was added to the preliminary mixture, and then butyl carbitol was added as needed to adjust the viscosity. Thus, the electroconductive paste was prepared. In Experimental Example 1, the curved portions 77 and the straight portions 78 were formed of the same electroconductive paste; hence the volume resistivity ratio $\rho1/\rho2$ was 1 at any temperature in the range of 700° C. to 900° C. The same applies to Experimental Examples 2 to 9. The electroconductive paste for the lead section 79 was prepared in the same manner as the electroconductive paste for the heating section 76 except that the alumina content and the Pt content were 2% by mass and 98% by mass, respectively.

Experimental Examples 10 to 18

Sensor elements 101 of Experimental Examples 10 to 18 were produced in the same as in Experimental Example 1 except that the volume resistivity ratio $\rho1/\rho2$ was varied as shown in Table 1. The volume resistivity ratio $\rho1/\rho2$ was varied by varying the Pt content in the lead side curved portion 77b. In any of Experimental Examples 10 to 18, widths W1 and W2 and thicknesses D1 and D2 were the same as in Experimental Example 1, and the cross-sectional area ratio S2/S1 was 1.00. In Experimental Examples 10 and 1, the cross-sectional area ratio S2/S1 and the volume resistivity ratio $\rho1/\rho2$ were the same.

The volume resistivity $\rho1$ in Experimental Examples 10 to 18 was measured using test pieces prepared as below. An insulating paste for the heater insulating layer 74 was applied by printing onto a ceramic green sheet that would be sintered into the second substrate layer 2. Subsequently, an electroconductive paste prepared under the same conditions as the respective electroconductive paste of the lead side curved portion 77b of Experimental Examples 10 to 18 was applied onto the insulating paste so as to form a rectangular parallelepiped. Then, the pastes were sintered under the same conditions as in Experimental Examples 10 to 18. The heating sections thus formed in the shape of a rectangular parallelepiped were used as test pieces of Experimental Examples 10 to 18. Leads for measuring resistance were connected to each rectangular parallelepipedal heating section. The resulting test piece was heated to 700° C. to 900° C. in an electric furnace, and the resistance of the heating section was measured in this state. Thus, volume resistivity ρ1 was calculated using the length of the rectangular parallelepipedal heating section, the cross-sectional area, and the measured resistance. Similarly, volume resistivity ρ2 was calculated from the results of measurement using the test piece. In Experimental Examples 10 to 18, the volume resistivity ratio ρ1/ρ2 hardly varied in the range of 700° C. to 900° C.

The durability (lifetime) of the heating section 76 of Experimental Examples 1 to 18 was examined. More specifically, a voltage was applied to the lead section 79 for supplying electricity to the heater 72 so that the heating section 76 would have a predetermined average temperature. Then, it was examined whether or not disconnection occurred in the heating section 76 within 2000 hours. When disconnection did not occur beyond 2000 hours, the durability was rated as "A (excellent, better than practical level)"; when disconnection occurred in the range of more than 1000 to 2000 or less, the durability was rated as "B (good, practical level)"; and when disconnection occurred within 1000 hours, the durability was rated as "C (failure, worse than practical level)". The durability of the heater 72 was examined in each of the cases in which the heating section 76 had an average temperature of 700° C., 750° C., 800° C., 850° C., and 900° C. The temperature of the heating section 76 was controlled by varying the voltage to be applied to the lead section 79. The temperature of the heating section 76 was indirectly measured by measuring the bottom temperature of the sensor element 101 with a radiation thermometer. The results of the examinations are shown in Table 1. Table 1 also shows the unit resistance ratio R1/R2, the cross-sectional area ratio S2/S1, and the volume resistivity ratio ρ1/ρ2 of each Experimental Example. The unit resistance ratio R1/R2 was calculated as the product of the cross-sectional area ratio S2/S1 and the volume resistivity ratio ρ1/ρ2.

TABLE 1

| | Unit Resistance Ratio R1/R2 | Cross-Sectional Area Ratio S2/S1 | Volume Resistivity Ratio ρ1/ρ2 | Average Temperature of Heating Section (° C.) | | | | |
|---|---|---|---|---|---|---|---|---|
| | | | | 700 | 750 | 800 | 850 | 900 |
| Experimental Example 1 | 1.00 | 1.00 | 1.00 | C | C | C | C | C |
| Experimental Example 2 | 0.95 | 0.95 | 1.00 | C | C | C | C | C |
| Experimental Example 3 | 0.91 | 0.91 | 1.00 | C | C | C | C | C |
| Experimental Example 4 | 0.87 | 0.87 | 1.00 | A | B | B | B | B |
| Experimental Example 5 | 0.83 | 0.83 | 1.00 | A | A | B | B | B |
| Experimental Example 6 | 0.80 | 0.80 | 1.00 | A | A | A | A | A |
| Experimental Example 7 | 0.77 | 0.77 | 1.00 | A | A | A | A | A |
| Experimental Example 8 | 0.74 | 0.74 | 1.00 | A | A | A | A | A |
| Experimental Example 9 | 0.71 | 0.71 | 1.00 | A | A | A | A | A |
| Experimental Example 10 | 1.00 | 1.00 | 1.00 | C | C | C | C | C |
| Experimental Example 11 | 0.95 | 1.00 | 0.95 | C | C | C | C | C |
| Experimental Example 12 | 0.91 | 1.00 | 0.91 | C | C | C | C | C |
| Experimental Example 13 | 0.87 | 1.00 | 0.87 | A | B | B | B | B |
| Experimental Example 14 | 0.83 | 1.00 | 0.83 | A | A | B | B | B |
| Experimental Example 15 | 0.80 | 1.00 | 0.80 | A | A | A | A | A |
| Experimental Example 16 | 0.77 | 1.00 | 0.77 | A | A | A | A | A |
| Experimental Example 17 | 0.74 | 1.00 | 0.74 | A | A | A | A | A |
| Experimental Example 18 | 0.71 | 1.00 | 0.71 | A | A | A | A | A |

A: Excellent,
B: Good,
C: Failure

Table 1 shows that disconnection in the heater 72 is less likely to occur as the unit resistance R1/R2 decreases. It was also observed that disconnection in the heater 72 is less likely to occur even at high temperatures as the unit resistance R1/R2 decreases. In Experimental Examples 4 to 9 and 13 to 18 in which the unit resistance ratio R1/R2 was set to 0.87 or less, the examination results were rated as A (excellent) or B (good) at any temperature in the range of 700° C. to 900° C. In Experimental Examples 6 to 9 and 15 to 18 in which the unit resistance ratio R1/R2 was set to 0.80 or less, the examination results were rated as A (excellent) at any temperature in the range of 700° C. to 900° C. In any of the Experimental Examples rated as B (good) or C (failure), disconnection occurred in the lead side curved portion 77b. The comparison between Experimental Examples 1 to 9 and Experimental Examples 10 to 18 shows that the examples in which the unit resistance ratio R1/R2 was the same as each other produced the same results between the case of varying the cross-sectional area ratio S2/S1 and the case of varying the volume resistivity ratio ρ1/ρ2. When the cross-sectional area ratio S2/S1 was varied by varying the thickness D1 of the lead side curved portion 77b, the same results as in Experimental Examples 1 to 9 were produced.

The present application claims priority from Japanese Patent Application No. 2015-164211 filed on Aug. 21, 2015, the entire contents of which are incorporated herein by reference.

What is claimed is:
1. A ceramic heater comprising:
   a plate-like ceramic body having a longitudinal direction and a short-length direction; and
   a heating element disposed within the plate-like ceramic body, the heating element including a lead section and a heating section connected to the lead section, wherein:

the heating section includes a plurality of curved portions and a plurality of straight portions, each of the plurality of straight portions having a length direction along the longitudinal direction, the plurality of curved portions including at least one lead side curved portion connected to two ends of two of the plurality of straight portions, the two ends being closer to the lead section than to opposite ends of the plurality of straight portions away from the lead section, wherein the at least one lead side curved portion includes a closest lead side curved portion that is closest to the lead section among the at least one lead side curved portion has a lower resistance per unit length than the plurality of straight portions at a temperature in a range of 700° C. to 900° C. and a unit resistance ratio R1/R2 of unit resistance R1 ($\mu\Omega$/mm), being the resistance per unit length of the closest lead side curved portion, to unit resistance R2 ($\mu\Omega$/mm), being the resistance per unit length of the plurality of straight portions, is no larger than 0.87 at a temperature in the range of 700° C. to 900° C. wherein a cross section of the closest lead side curved portion, taken in a direction perpendicular to a length direction thereof, has a larger area than a cross section of the plurality of straight portions, taken in a direction perpendicular to a length direction thereof, and a cross sectional area ratio S2/S1 of the area S2 (mm$^2$) of the cross section of the plurality of straight portions to the area SI (mm$^2$) of the cross section of the closest lead side curved portion is no larger than 0.87.

2. The ceramic heater according to claim 1, wherein the unit resistance ratio R1/R2 is no larger than 0.80 at a temperature in the range of 700° C. to 900° C.

3. The ceramic heater according to claim 1, wherein the cross sectional area ratio S2/S1 is no larger than 0.80.

4. The ceramic heater according to claim 1, wherein the closest lead side curved portion has a lower volume resistivity than the straight portion at a temperature in the range of 700° C. to 900° C.

5. The ceramic heater according to claim 4, wherein a volume resistivity ratio $\rho1/\rho2$ of the volume resistivity $\rho1$ ($\mu\Omega\cdot$cm) of the closest of the at least one lead side curved portion to the volume resistivity $\rho2$ ($\mu\Omega\cdot$cm) of the straight portion is no larger than 0.87 at a temperature in the range of 700° C. to 900° C.

6. The ceramic heater according to claim 5, wherein the volume resistivity ratio $\rho1/\rho2$ is no larger than 0.80 at a temperature in the range of 700° C. to 900° C.

7. The ceramic heater according to claim 1, wherein the plurality of straight portions includes four or more straight portions arranged along the short-length direction, and the at least one lead side curved portion connects a pair of the straight portions adjacent to each other in the short-length direction at one of the ends of each adjacent straight portion closer to the lead section, and wherein the heating section includes a plurality of non-lead side curved portions, each connecting a pair of the straight portions adjacent to each other in the short-length direction at one of the ends of each adjacent straight portion far from the lead section.

8. A ceramic heater comprising:
a plate-like ceramic body having a longitudinal direction and a short-length direction; and
a heating element disposed within the plate-like ceramic body, the heating element including a lead section having a positive lead and a heating section connected to the lead section, wherein:

the heating section includes a plurality of curved portions and a plurality of straight portions, each of the plurality of straight portions having a length direction along the longitudinal direction, the plurality of curved portions including at least one lead side curved portion connected to two ends of two of the plurality of straight portions, the two ends being closer to the lead section than to opposite ends of the plurality of straight portions away from the lead section, wherein the at least one lead side curved portion includes a closest lead side curved portion that is closest to the positive lead among the at least one lead side curved portion has a lower resistance per unit length than the plurality of straight portions at a temperature in a range of 700° C. to 900° C. and a unit resistance ratio R1/R2 of unit resistance R1 ($\mu\Omega$/mm), being the resistance per unit length of the closest lead side curved portion, to unit resistance R2 ($\mu\Omega$/mm), being the resistance per unit length of the plurality of straight portions, is no larger than 0.87 at a temperature in the range of 700° C. to 900° C., and wherein a cross section of the closest lead side curved portion, taken in a direction perpendicular to a length direction thereof, has a larger area than a cross section of the plurality of straight portions, taken in a direction perpendicular to a length direction thereof, and a cross sectional area ratio S2/S1 of the area S2 (mm$^2$) of the cross section of the plurality of straight portions to the area SI (mm$^2$) of the cross section of the closest lead side curved portion is no larger than 0.87.

9. The ceramic heater according to claim 8, wherein the unit resistance ratio R1/R2 is no larger than 0.80 at a temperature in the range of 700° C. to 900° C.

10. The ceramic heater according to claim 8, wherein the closest lead side curved portion has a lower volume resistivity than the straight portion at a temperature in the range of 700° C. to 900° C.

11. The ceramic heater according to claim 8, wherein the plurality of straight portions includes four or more straight portions arranged along the short-length direction, and the at least one lead side curved portion connects a pair of the straight portions adjacent to each other in the short-length direction at one of the ends of each adjacent straight portion closer to the lead section, and wherein the heating section includes a plurality of non-lead side curved portions, each connecting a pair of the straight portions adjacent to each other in the short-length direction at one of the ends of each adjacent straight portion far from the lead section.

* * * * *